(12) United States Patent
Winter et al.

(10) Patent No.: US 11,596,357 B2
(45) Date of Patent: Mar. 7, 2023

(54) SLEEP STUDY SYSTEM AND METHOD

(71) Applicant: KONINKLIJKE PHILIPS N.V., Eindhoven (NL)

(72) Inventors: Stefan Winter, Würselen (DE); Edmund Arnliot Shaw, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1288 days.

(21) Appl. No.: 15/780,271

(22) PCT Filed: Nov. 24, 2016

(86) PCT No.: PCT/EP2016/078607
§ 371 (c)(1),
(2) Date: May 31, 2018

(87) PCT Pub. No.: WO2017/093098
PCT Pub. Date: Jun. 8, 2017

(65) Prior Publication Data
US 2018/0353131 A1    Dec. 13, 2018

Related U.S. Application Data

(60) Provisional application No. 62/261,366, filed on Dec. 1, 2015.

(30) Foreign Application Priority Data

Dec. 22, 2015    (EP) .................................... 15201944

(51) Int. Cl.
G08B 21/00    (2006.01)
A61B 5/00    (2006.01)
(Continued)

(52) U.S. Cl.
CPC .......... *A61B 5/6843* (2013.01); *A61B 5/4812* (2013.01); *A61B 5/4818* (2013.01);
(Continued)

(58) Field of Classification Search
CPC ... A61B 5/6843; A61B 5/4812; A61B 5/4818; A61B 5/02416; A61B 5/318; A61B 5/369
(Continued)

(56) References Cited

U.S. PATENT DOCUMENTS 6,421,554 B1    7/2002  Lee et al.
6,928,031 B1    8/2005  Kanevsky et al.
(Continued)

FOREIGN PATENT DOCUMENTS

DE    4209336 A1    9/1993
EP    2583248 B1    10/2018
(Continued)

*Primary Examiner* — Mark S Rushing

(57) ABSTRACT

A sleep study system comprises a set of sensors for monitoring physiological parameters of a subject during sleep as part of a sleep study and for monitoring the sleep stage of the subject. It is determined if intervention to the subject is needed for maintenance or repair to the sleep study system. If so, a time to perform the intervention is also derived based on the sleep stage of the subject, in particular so as to be least disruptive to the subject.

15 Claims, 3 Drawing Sheets

(51) Int. Cl.
*A61B 5/024* (2006.01)
*A61B 5/318* (2021.01)
*A61B 5/369* (2021.01)

(52) U.S. Cl.
CPC ........... *A61B 5/02416* (2013.01); *A61B 5/318* (2021.01); *A61B 5/369* (2021.01)

(58) Field of Classification Search
USPC .......................................... 340/575; 702/19
See application file for complete search history.

(56) References Cited

U.S. PATENT DOCUMENTS

| | | | |
|---|---|---|---|
| 8,876,737 B2 | 11/2014 | Behan et al. | |
| 8,948,861 B2 | 2/2015 | Rai et al. | |
| 8,994,542 B2 | 3/2015 | Sakai | |
| 9,294,732 B2 | 3/2016 | Gillette | |
| 10,595,772 B2 | 3/2020 | Burton | |
| 2006/0122863 A1* | 6/2006 | Gottesman | G16H 10/60 705/2 |
| 2007/0249952 A1 | 10/2007 | Rubin | |
| 2008/0053441 A1* | 3/2008 | Gottlib | A61M 16/12 128/204.23 |
| 2011/0275960 A1 | 11/2011 | Westerink et al. | |
| 2012/0157873 A1 | 6/2012 | Liang et al. | |
| 2014/0049627 A1* | 2/2014 | Gillette | A61B 5/7225 348/77 |
| 2014/0194759 A1 | 7/2014 | Weiland et al. | |
| 2015/0136125 A1* | 5/2015 | Colla | A61M 16/0003 128/202.22 |
| 2015/0173672 A1* | 6/2015 | Goldstein | A61B 5/6898 600/301 |
| 2016/0007931 A1 | 1/2016 | Rubin | |
| 2016/0151603 A1* | 6/2016 | Shouldice | H04R 3/00 600/26 |

FOREIGN PATENT DOCUMENTS

| | | |
|---|---|---|
| GB | 2447640 A | 9/2008 |
| JP | 2015097636 A | 5/2015 |
| RU | 2061406 C1 | 6/1996 |
| WO | 2009128000 A1 | 10/2009 |
| WO | 2014118693 A1 | 8/2014 |

\* cited by examiner

SLEEP STUDY SYSTEM AND METHOD

CROSS-REFERENCE TO PRIOR APPLICATIONS

This application is the U.S. National Phase application under 35 U.S.C. § 371 of International Application Serial No. PCT/EP2016/078607, filed on 24 Nov. 2016, which claims the benefit of U.S. Application Ser. No. 62/261,366, filed on 1 Dec. 2015, and European Application No. 15201944.4, filed on 22 Dec. 2015. These applications are hereby incorporated by reference herein.

FIELD OF THE INVENTION

The invention relates to systems for performing overnight sleep studies of a subject.

BACKGROUND OF THE INVENTION

It is well known that poor or inadequate sleep is both prevalent and medically undesirable. It is known that sleep habits can be improved, assuming the patient is aware of the current quality of his or her sleep.

By providing feedback regarding the sleep quality, patients may enact behavioral changes and/or adjust sleep habits in a way that promotes improved sleep quality. It is known that an indication of sleep quality may require identification of different sleep stages during sleep, as well as transitions therebetween. It is known that the sleep stages commonly include a rapid eye movement (REM) stage and one or more non rapid eye movement stages (NREMs).

It is also well known that polysomnography (PSG) may be used to analyze, detect, and/or determine the current sleep stage of a subject. Such analysis for example takes place as part of a sleep study.

During overnight sleep studies, various incidents can occur that require an intervention to fix them and ensure high-quality measurements. A typical example is a sensor that has fallen off due to a patient's movement. Existing PSG systems can detect a number of incidents and provide an alarm based on missing or unrealistic measurement values routed to a separate control room.

In addition, overnight sleep studies usually involve cameras to observe the room and patient, which allows an attending sleep technician to notice incidents visually. Typically, the sleep technician subsequently enters the patient's room and resolves the issue.

While the above described approach ensures high-quality measurements from a technical point of view because the uptime of the PSG system is maximized, the resolution of issues might also interfere with the patient's sleep. Due to the environment the patient is in, this sleep is already sub-optimal and should not be further disturbed.

SUMMARY OF THE INVENTION

The invention is defined by the claims.

According to examples in accordance with an aspect of the invention, there is provided a sleep study system, comprising:

a set of sensors for monitoring physiological parameters of a subject during sleep as part of a sleep study and for monitoring the sleep stage of the subject;

a processor adapted to:

determine from outputs of the set of sensors that there is sensor malfunction or sensor disconnection so that intervention to the subject is needed for maintenance or repair to the sleep study system; and determine from the outputs of the set of sensors a time to perform the intervention in dependence on the sleep stage of the subject, and provide an output relating to the time to perform the intervention.

This system for example provides real-time optimal timing for an intervention that minimizes the potential sleep disturbance, leading to overall higher quality results of the sleep study. Thus, the time to perform the intervention is one which is least disruptive to the subject.

The system is able to detect incidents that require an intervention and generate a related output such as an alarm. The current sleep stage is also determined in real-time. Based on the sleep stage the optimal time takes account of how appropriate an intervention at a given time would be, as waking up the patient during some sleep stages is less disturbing than during other sleep stages.

The set of sensors may comprise a first set of sensors for monitoring the physiological parameters of the subject during sleep and a second set of sensors for monitoring the sleep stage, wherein the first set and the second set are mutually exclusive.

For example, the first set of sensors may monitor such parameters as the oxygen level in the blood, the heart rate, the breathing rate, as well as eye and arm and/or leg movements. The second set of sensors may for example comprise EEG sensors.

The set of sensors may comprises a first set of sensors for monitoring the physiological parameters of a subject during sleep and a second set of sensors for monitoring the sleep stage, wherein the second set is a sub-set of the first set.

For example the second set may comprise EEG sensors, which are also used as part of the sleep study. The first set may then comprise a selection from sensors which monitor such parameters as the oxygen level in the blood, the heart rate, the breathing rate, eye and leg movements and the EEG. In this way, the optimal timing indication does not require any additional sensors to be used than those already present for the sleep study.

The intervention may for example be needed if a sensor (of the first set) malfunctions or falls off the subject. This will be detected based on the sensor output.

The set of sensors thus may comprise at least an EEG sensor for monitoring the sleep stage. A PPG sensor may be used for monitoring heart rate and/or respiration. The sensors together may enable a polysomnography system to be implemented.

The output indicating the time to perform the intervention may comprise:

an output at the time to perform the intervention; and/or an output in advance of the time to perform the intervention which gives a prediction of the time to perform the intervention.

Thus, a user of the system may be told when intervention is appropriate, either at the time, or in advance of the time, or both.

The processor may be further adapted to determine an expected time to the end of sleep or the end of the sleep study and to take this into account when determining the time to perform the intervention.

Examples in accordance with another aspect of the invention also provide a sleep study method, comprising:

monitoring physiological parameters of a subject during sleep and monitoring the sleep stage of the subject using a set of sensors;

determining from the outputs of the set of sensors that there is sensor malfunction or sensor disconnection so that intervention to the subject is needed for maintenance or repair to the sleep study system; and determining from the outputs of the set of sensors a time to perform the intervention in dependence on the sleep stage of the subject, and providing an output relating to the time to perform the intervention.

This method enables a sleep study system to be maintained during a sleep study in a way which is least likely to arouse the patient and therefore potentially influence the sleep study results.

The monitoring may comprise:

using a first set of sensors to monitor the physiological parameters of a subject during sleep and using a second set of sensors to monitor the sleep stage, wherein the first set and the second set are mutually exclusive.

The monitoring may instead comprise:

using a first set of sensors to monitor the physiological parameters of a subject during sleep and using a second set of sensors to monitor the sleep stage, wherein the second set is a sub-set of the first set.

The monitoring may comprise EEG monitoring of the sleep stage and/or PPG monitoring.

Providing an output indicating the time to perform the intervention may comprise:

providing an output at the time to perform the intervention; and/or providing an output in advance of the time to perform the intervention which gives a prediction of the time to perform the intervention.

An expected time to the end of sleep may also be determined and this can be taken into account when determining the time to perform the intervention.

The invention may be implemented as least in part in software.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a sleep study system, comprising a set of sensors for monitoring physiological parameters of a subject during sleep as part of a sleep study and for monitoring the sleep stage of the subject. It is determined if intervention to the subject is needed for maintenance or repair to the sleep study system. If so, a time to perform the intervention is also derived based on the sleep stage of the subject, in particular so as to be least disruptive to the subject.

The sleep study may be a polysomnography study, which is used to diagnose, or rule out, many types of sleep disorders including narcolepsy, idiopathic hypersomnia, periodic limb movement disorder (PLMD), REM behavior disorder, parasomnias, and sleep apnea.

In a typical polysomnography study, brain waves are recorded using an EEG (electroencephalogram) sensor, the oxygen level in the blood is recorded using a PPG (photoplethysmogram) sensor, the heart rate and breathing rate are recorded using PPG and/or ECG (electrocardiogram) sensors, as well as eye and leg movements during the study, using optical sensors, accelerometers or other sensors.

The type of information which is monitored for the sleep study depends on its purpose. One common purpose is for diagnosing sleep apnea, where the main information to be obtained are the occurrences of apneas and hypopneas derived, determined from breathing sensors and PPG sensors. The required set of sensors for this type of sleep study is for example integrated as part of a home sleep test system, which does not require EEG sensing. This is also a very common type of sleep study in sleep laboratories, in which case a larger parameter set is sensed.

The sleep study may include sensors which enable monitoring of the sleep stage. Alternatively, additional sensors may be provided for monitoring the sleep stage as separate information to the sleep study, if the sleep study sensors are for a different purpose.

Different sensors can be used to give an indication of sleep stages for example EEG sensors, ECG sensors and PPG sensors. Thus even if EEG sensors which are primarily used for detecting sleep stages fall off, or otherwise become non-functioning, others sensors which are present as part of the sleep study may be used to continue to determine the sleep stage.

During sleep, subjects commonly alternate between a random eye movement (REM) stage and three or four different NREM stages, depending on the models and/or definitions used. NREM stages are usually referred to as stage 1 through stage 3 or stage 4, as appropriate. Through sleep staging, a pattern of stages may be obtained for a subject.

Figure 1:
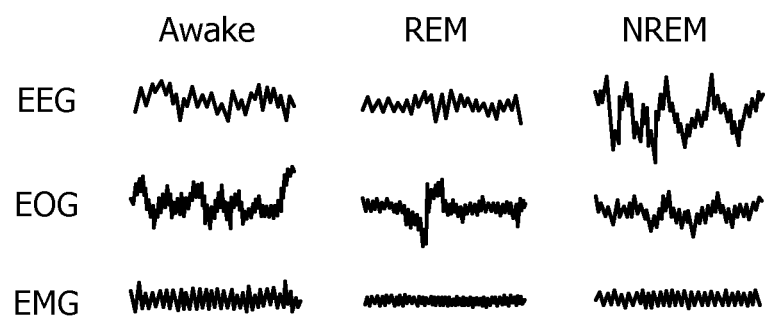
FIG. 1 shows a set of signals used for sleep staging.

FIG. 1 shows the characteristic features of brain activity in various sleep stages. In particular, FIG. 1 shows common exemplary graphs for an EEG study (Electroencephalography), an EOG study (Electrooculography), and an EMG study (Electromyography) during wakefulness, REM stage and NREM stages.

The EEG measures electrical brain activity, the EOG measures eye movement and the EMG measures muscle activity, for example using a surface electrode or electrode array.

Commonly, EEG signals for example may be measured and/or received using one or more electrodes positioned on the head of a subject. The amplitude of these signals, as well as the specifics of the peaks, troughs, sleep spindles, k-complexes, slow waves, and/or frequency-based characteristics within these signals may be analyzed to distinguish the current sleep stage of a subject. For example, slow waves are known to be more abundant in sleep stage 3 and sleep stage 4, whereas sleep spindles may be more abundant in sleep stage 2.

Figure 2:
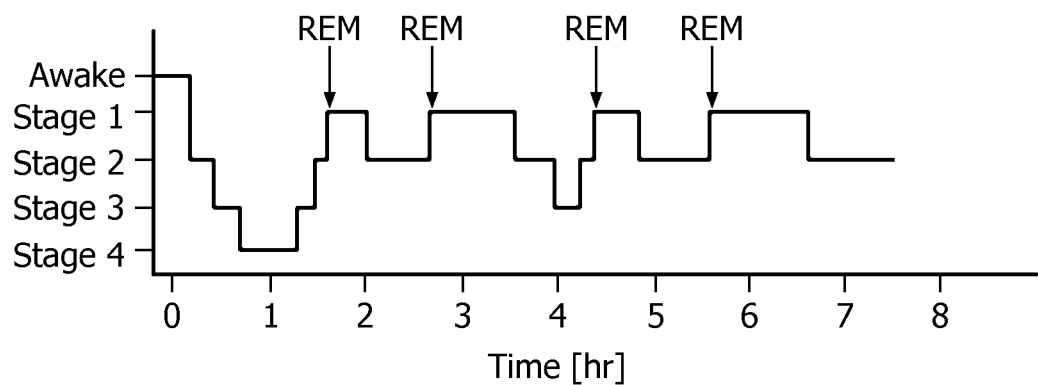
FIG. 2 shows how different sleep stages may arise during a night.
Figure 3:
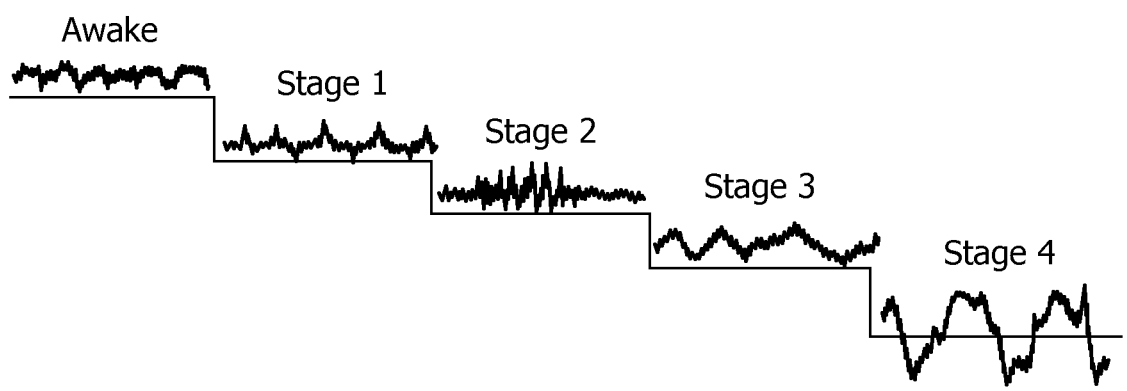
FIG. 3 shows a part of FIG. 2 in more detail.

FIG. 2 illustrates the progress of a subject through five sleep stages through a period of approximately 8 hours of sleep, as recorded through an EEG. FIG. 3 illustrates approximately the first two hours depicted in FIG. 2 in more detail. For example, FIG. 3 depicts a sleep spindle during stage 2, in which the amplitude increases in the center of the sleep spindle. Analysis of the signals in FIGS. 1 and 2, for example frequency-based analysis, may be used to distinguish between different sleep stages, e.g. based on different characteristics per sleep stage.

There are various known systems for monitoring sleep stage, i.e. for sleep staging, not limited to the combination of EEG, EOG and EMG signals.

The most typical system makes use at least of an EEG signal as shown above, obtained using electrodes attached to the scalp. The measured brain activity even from an EEG signal alone can be classified into the NREM sleep stages (N1, N2, N3), the rapid eye movement REM stage and a wakefulness stage.

However, it has been suggested that other parameters may be used such as an ECG signal, and/or respiratory and body movement signals. For example, this is proposed in WO 2009/128000.

It is also known to provide stimuli to a subject and to use their response to provide an indication or validation of a sleep stage. This approach is for example disclosed in WO 2014/118693. In this system, sensory stimuli may include visual stimuli, auditory stimuli, tactile stimuli, olfactory stimuli, electromagnetic stimuli, somatosensory stimuli, other sensory stimuli and/or any combination and/or sequence thereof. A stimulus source may thus include one or more of a light source, a loudspeaker, an electroacoustic transducer, a vibrating component or device, a device or system configured to produce scents or electrodes.

The invention can make use of any known sensor arrangement for providing a determination of the sleep stage of a subject. Note that in this context a state of wakefulness is included as one of the sleep stages.

Figure 4:
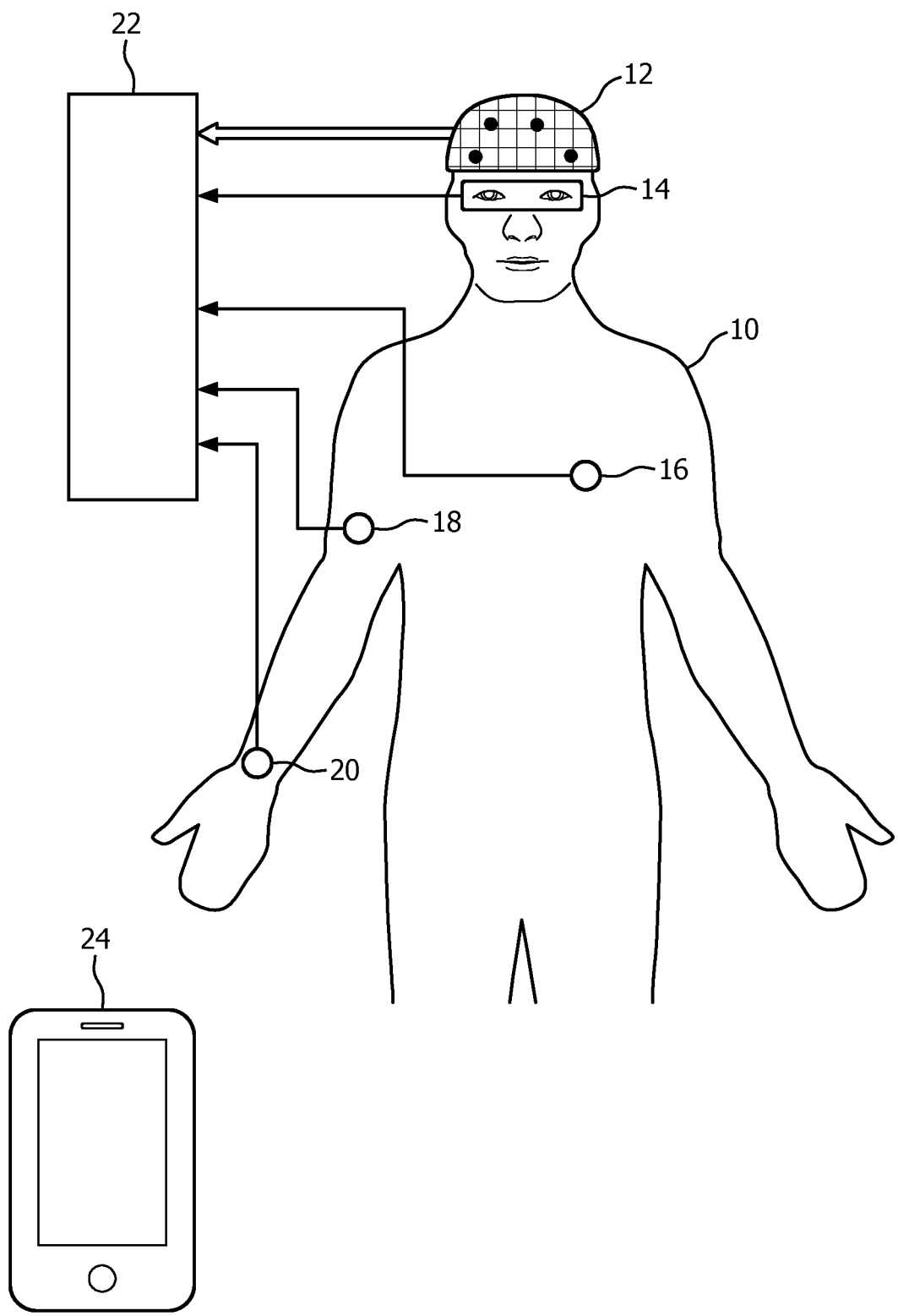
FIG. 4 shows a sleep study system.

FIG. 4 shows a sleep study system.

It comprises a set of sensors for monitoring physiological parameters of a subject 10 during sleep as part of a sleep study and for monitoring the sleep stage of the subject.

The sensors comprise an EEG sensor 12 in the form of a set of scalp electrodes, an EOG sensor 14 in the form of an optical system integrated into a pair of goggles, an ECG sensor 16, an EMG sensor 18 (in this example attached to an arm) a PPG sensor 20.

These are just examples of the types of sensor that may be used to gather physiological information about the subject. Other examples are accelerometers, effort belts (chest and abdomen), oral thermistors, nasal flow sensors, microphones.

The outputs from a subset of these sensors are able to be interpreted to provide sleep staging.

The typical set of channels recorded during a polysomnogram (PSG) has both redundancy and some sensor signals that are more important than others. For example, there are usually four or more EEG channels and two effort channels. While not ideal, a record could be scored with just one EEG channel and one effort channel.

Because sleep studies are typically conducted to assess sleep related breathing disorders, respiratory flow signals may be more important than leg EMG signals for example. A skilled sleep technician would not risk waking up a patient to correct EEG electrodes if there was still a usable EEG channel, but would rather wait for a natural awakening to go in and adjust the signal. However, if there was no usable flow channel, this merits disturbing the patient.

Note that sleep studies may be used for other purposes as well, not just for respiratory disorders. For example, if there is a suspicion of restless leg syndrome (RLS) leg EMG sensors are very important.

A processor 22 is adapted to determine from the outputs of the set of sensors that intervention to the subject is needed for maintenance or repair to the sleep study system.

This is typically when a sensor becomes detached from the subject or fails to function for any other reason. The processor 22 can detect this based on the signals received being inconsistent with normal signal capture.

The processor can then determine from the outputs of the set of sensors (i.e. those that are still correctly functioning) the current stage of sleep of the subject.

From this sleep stage information, an optimal time to perform the intervention can be derived, which is least disruptive to the subject.

The system has an output interface device 24 which is in this case is shown as a remote portable device such as a smart phone with which the processor communicates. It provides an alert that the system needs maintenance and also an indication of when the intervention is most appropriate. An output is provided indicating the optimal time.

This system provides real-time optimal timing for an intervention that minimizes the potential sleep disturbance, leading to overall higher-quality results of the sleep study.

Of course, it would be best to go into the room while a patient is awake. If not, there is a strong preference to avoid disturbing REM sleep, as there is less REM sleep during the night and breathing is often distinctly different from others stages of consciousness. During slow wave sleep (N3 & N4), patients are less likely to be roused by a technician entering the room. Thus, the intervention may be carried out when the subject is at N3 or N4 sleep stages. Manipulating a subject patient during these sleep stages is less disturbing and therefore less likely to result in awakening than during other sleep stages.

When to enter or not enter the room will in practice be driven by a decision matrix that assesses the urgency of correcting the signal. In particular, it is determined whether or not the study is usable without the signal, as well as the patient's level of consciousness.

The system can compensate for a lack of skilled sleep technologists by providing assistance to their decision making.

The sleep study may itself require the sleep stages to be identified, but this is not essential. Thus, in some cases, the sensors for the sleep study (a first set) are completely separate to those (a second set) needed to perform sleep staging. In other cases, the sensors overlap in that the sleep study includes, as a subset, sensors which can be used to provide sleep staging.

As is clear from FIG. 4, the set of sensors for the sleep study may monitor such parameters as the oxygen level in the blood (PPG sensor 20), the heart rate (ECG sensor 16), the breathing rate (PPG sensor 20 or other sensors not shown), as well as eye (OCG sensor 16) and arm or leg movements (EMG sensor 18). The second set of sensors may for example comprise EEG sensors (EEG sensor cap 12).

The output indicating the optimal time may be provided at the suitable time, i.e. when the sleep stage reaches the preferred stage. However, based on the analysis of the sleep pattern up to that point, an estimation may also be made as to when the sleep stage is likely to reach that stage. Thus, an alarm can be given that maintenance is needed as well as an estimate of when the maintenance should be carried out. When the actual desired sleep stage is reached, a further alert may be provided. The processor may also determine an expected time to the end of sleep and take this into account when determining the optimal time.

More generally, in addition to sleep staging, other factors may be taken into account, of which the time until the end of the sleep study is one example. All the information can be then be combined to determine when best to solve an issue. The decision may also be based on a ranking of importance of various detected incidents and their combinations. For example, only if a certain importance level threshold related to a certain sleep stage is passed will an alarm be raised.

The output device can show the current sleep stage and can show the results of a predictive algorithm, for example based on small but relevant changes in the sleep pattern that can be used to predict an upcoming change in the sleep stage. As mentioned above, this can be used to predict when in the future solving an issue would be appropriate.

The output device may be a fixed part of a system, for example in a control room at which the sleep study is monitored. Thus, it does not need to be a separate remote device as shown.

Figure 5:
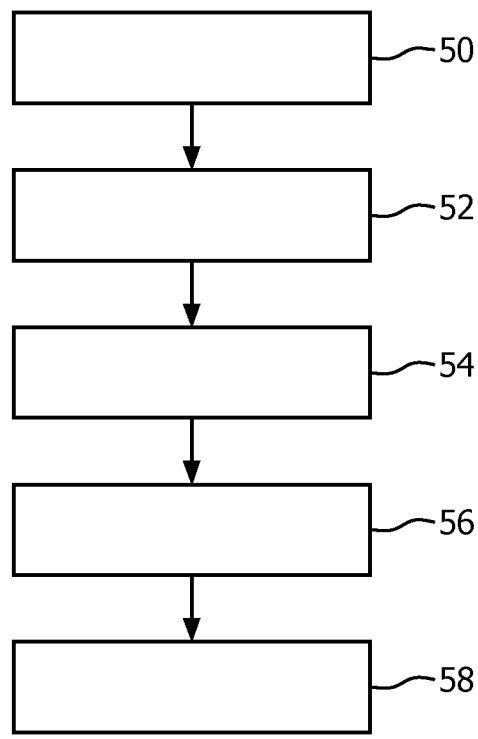
FIG. 5 shows a sleep study method.

FIG. 5 shows a sleep study method, comprising monitoring physiological parameters of a subject during sleep in step 50. These parameters are used in step 52 to determine a sleep stage of the subject.

In step 54, it is determined that intervention to the subject is needed for maintenance or repair to the sleep study system. This is based on anomalies in the signals received from one or more sensors.

In step 56, an optimal time is determined to perform the intervention to be least disruptive to the subject.

In step 58 an output is provided indicating the optimal time. It may be provided at the optimal time, or in advance of the optimal time, or both.

This method enables a sleep study system to be maintained during a sleep study in a way which is least likely to arouse the patient and therefore potentially influence the sleep study results.

Figure 6:
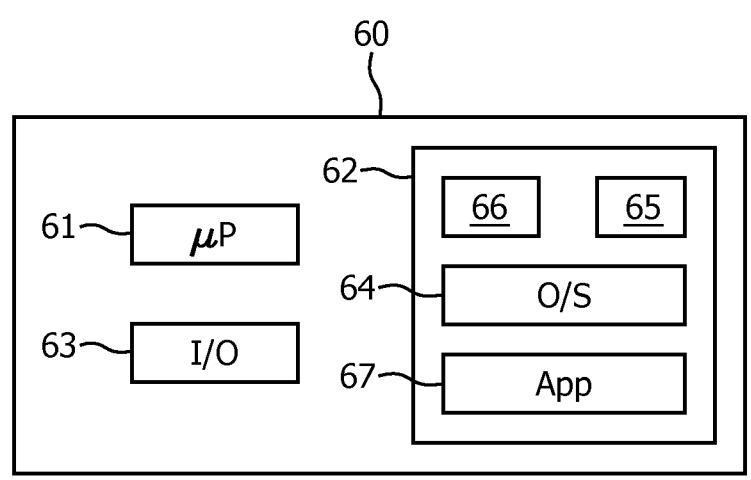
FIG. 6 shows a general computer architecture, suitable for performing the signal processing.

The processor 22 implements an algorithm for processing the sensor data. FIG. 6 illustrates an example of a computer 60 for implementing the processor.

The computer 60 includes, but is not limited to, PCs, workstations, laptops, PDAs, palm devices, servers, storages, and the like. Generally, in terms of hardware architecture, the computer 60 may include one or more processors 61, memory 62, and one or more I/O devices 63 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 61 is a hardware device for executing software that can be stored in the memory 62. The processor 61 can be virtually any custom made or commercially available processor, a central processing unit (CPU), a digital signal processor (DSP), or an auxiliary processor among several processors associated with the computer 60, and the processor 61 may be a semiconductor based microprocessor (in the form of a microchip) or a microprocessor.

The memory 62 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 62 may incorporate electronic, magnetic, optical, and/or other types of storage media. Note that the memory 62 can have a distributed architecture, where various components are situated remote from one another, but can be accessed by the processor 61.

The software in the memory 62 may include one or more separate programs, each of which comprises an ordered listing of executable instructions for implementing logical functions. The software in the memory 62 includes a suitable operating system (O/S) 64, compiler 65, source code 66, and one or more applications 67 in accordance with exemplary embodiments.

The application 67 comprises numerous functional components such as computational units, logic, functional units, processes, operations, virtual entities, and/or modules.

The operating system 64 controls the execution of computer programs, and provides scheduling, input-output control, file and data management, memory management, and communication control and related services.

Application 67 may be a source program, executable program (object code), script, or any other entity comprising a set of instructions to be performed. When a source program, then the program is usually translated via a compiler (such as the compiler 65), assembler, interpreter, or the like, which may or may not be included within the memory 62, so as to operate properly in connection with the operating system 64. Furthermore, the application 67 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 63 may include input devices such as, for example but not limited to, a mouse, keyboard, scanner, microphone, camera, etc. Furthermore, the I/O devices 67 may also include output devices, for example but not limited to a printer, display, etc. Finally, the I/O devices 63 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 63 also include components for communicating over various networks, such as the Internet or intranet.

When the computer 60 is in operation, the processor 61 is configured to execute software stored within the memory 62, to communicate data to and from the memory 62, and to generally control operations of the computer 60 pursuant to the software. The application 67 and the operating system 64 are read, in whole or in part, by the processor 61, perhaps buffered within the processor 61, and then executed.

When the application 67 is implemented in software it should be noted that the application 67 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The example above is primarily aimed at preventing the patient be woken. However, there are times when intervention is needed and the subject should be woken—for example for their wellbeing or safety. In this case, the sleep stage can be chosen in such a way that waking the subject is least disruptive. This will be at a different time to intervention when the patient is not to be aroused.

By way of example the concept of arousing a subject at an optimal time is discussed in U.S. Pat. No. 8,876,737. It is suggested that arousal may take place during N1 and N2 stages of sleep. Thus, the system of this application may define the optimal time as N1 and N2 if it is determined that the patient is to be awoken.

Thus, the term "least disruptive to the subject" may include deliberately awakening them or deliberately not awakening them.

The examples above are based on detected sensor failure and determining when to intervene. In addition, an optimal time for intervention may be based on a predicted sensor failure rather than a detected sensor failure. In this way, if sensor failure is predicted, the actual failure could be prevented by pre-emptively exchanging or reattaching the sensor. For example, such a prediction could be based on a gradual degradation of data quality, where the current data quality is still sufficient to obtain the desired information but the data quality trend shows that this will not be the case in the near future. By way of example, a flow sensor may be slowly falling off, resulting in a decreasing flow amplitude despite the effort belts showing an unchanging breathing effort.

Thus "determining that intervention to the subject is needed for maintenance or repair to the sleep study system" includes detecting sensor failure or detecting sensor signal degradation which is indicative of future sensor failure. It may include any other sensor adaptations or adjustments needed during the sleep study.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A sleep study system, comprising:
a set of sensors for monitoring physiological parameters of a subject during sleep as part of a sleep study and for monitoring the sleep stage of the subject;
a processor adapted to:
determine from outputs of the set of sensors that there is sensor malfunction or sensor disconnection so that intervention to the subject is needed for maintenance or repair to the sleep study system; and
determine from the outputs of the set of sensors a time to perform the intervention in dependence on the sleep stage of the subject, and provide an output relating to the time to perform the intervention.

2. A system as claimed in claim 1, wherein the set of sensors comprises:
a first set of sensors for monitoring the physiological parameters of a subject during sleep and a second set of sensors for monitoring the sleep stage, wherein the first set and the second set are mutually exclusive.

3. A system as claimed in claim 1, wherein the set of sensors comprises:
a first set of sensors for monitoring the physiological parameters of a subject during sleep and a second set of sensors for monitoring the sleep stage, wherein the second set is a sub-set of the first set.

4. A system as claimed in claim 1, wherein the set of sensors comprises at least an EEG sensor for monitoring the sleep stage.

5. A system as claimed in claim 1, wherein the set of sensors comprises at least a PPG sensor and wherein the sleep study system is a polysomnography system.

6. A system as claimed in claim 1, wherein the output relating to the time to perform the intervention comprises:
an output at the time to perform the intervention; and/or
an output in advance of the time to perform the intervention which gives a prediction of the time.

7. A system as claimed in claim 1, wherein the processor is further adapted to determine an expected time to the end of sleep and to take this into account when determining the time to perform the intervention.

8. A sleep study method, comprising:
monitoring physiological parameters of a subject during sleep and monitoring the sleep stage of the subject using a set of sensors;
determining from the outputs of the set of sensors that there is sensor malfunction or sensor disconnection so that intervention to the subject is needed for maintenance or repair to the sleep study system; and
determining from the outputs of the set of sensors a time to perform the intervention in dependence on the sleep stage of the subject, and providing an output relating to the time to perform the intervention.

9. A method as claimed in claim 8, wherein the monitoring comprises:
using a first set of sensors to monitor the physiological parameters of a subject during sleep and using a second set of sensors to monitor the sleep stage, wherein the first set and the second set are mutually exclusive.

10. A method as claimed in claim 8, wherein the monitoring comprises:
using a first set of sensors to monitor the physiological parameters of a subject during sleep and using a second set of sensors to monitor the sleep stage, wherein the second set is a sub-set of the first set.

11. A method as claimed in claim 8, wherein the monitoring comprises EEG monitoring of the sleep stage and/or PPG monitoring.

12. A method as claimed in claim 8, wherein the sleep study is a polysomnography study.

13. A method as claimed in claim 8, wherein providing an output relating to the time to perform the intervention comprises:
providing an output at the time to perform the intervention; and/or
providing an output in advance of the time to perform the intervention which gives a prediction of the time to perform the intervention.

14. A method as claimed in claim 8, comprising determining an expected time to the end of sleep and taking this into account when determining the time to perform the intervention.

15. A non-transitory machine-readable storage medium having stored thereon instructions which, when executed on a processor, performs computer program comprises computer program code means adapted, when said program is run on a computer, to perform the method of claim 8.

* * * * *